United States Patent
Artzi et al.

(10) Patent No.: US 9,877,984 B2
(45) Date of Patent: Jan. 30, 2018

(54) CONTROLLABLY DEGRADABLE COMPOSITIONS AND METHODS

(71) Applicant: Massachusetts Institute of Technology, Cambridge, MA (US)

(72) Inventors: Natalie Artzi, Brookline, MA (US); Elazer R. Edelman, Brookline, MA (US); Regina Kelmansky, Haifa (IL); Marc Mier Cervantes, Sant Cugat del Valles (ES)

(73) Assignee: Massachusetts Institute of Technology, Cambridge, MA (US)

( * ) Notice: Subject to any disclaimer, the term of this patent is extended or adjusted under 35 U.S.C. 154(b) by 93 days.

(21) Appl. No.: 14/581,208

(22) Filed: Dec. 23, 2014

(65) Prior Publication Data

US 2015/0174156 A1    Jun. 25, 2015

Related U.S. Application Data

(60) Provisional application No. 61/920,217, filed on Dec. 23, 2013.

(51) Int. Cl.
| | |
|---|---|
| A61K 31/785 | (2006.01) |
| A61K 47/34 | (2017.01) |
| A61L 27/20 | (2006.01) |
| A61L 27/50 | (2006.01) |
| A61K 9/00 | (2006.01) |
| A61L 24/00 | (2006.01) |
| A61L 24/08 | (2006.01) |

(52) U.S. Cl.
CPC .......... *A61K 31/785* (2013.01); *A61K 9/0019* (2013.01); *A61K 47/34* (2013.01); *A61L 24/001* (2013.01); *A61L 24/08* (2013.01); *A61L 27/20* (2013.01); *A61L 27/50* (2013.01)

(58) Field of Classification Search
None
See application file for complete search history.

(56) References Cited

U.S. PATENT DOCUMENTS

| | | | |
|---|---|---|---|
| 4,731,162 A | 3/1988 | Solarek et al. | |
| 5,612,321 A | 3/1997 | Nguyen | |
| 6,288,043 B1 | 9/2001 | Spiro et al. | |
| 6,949,524 B2 | 9/2005 | Singh et al. | |
| 7,985,424 B2 | 7/2011 | Tomalia et al. | |
| 8,252,834 B2 | 8/2012 | Baker, Jr. et al. | |
| 8,382,889 B1 | 2/2013 | Brizius | |
| 8,404,779 B2 | 3/2013 | Chenault | |
| 8,426,492 B2 | 4/2013 | Lu | |
| 8,431,114 B2 | 4/2013 | Kodokian et al. | |
| 2005/0002893 A1 | 1/2005 | Goldmann | |
| 2006/0078536 A1* | 4/2006 | Kodokian | A61K 31/785 |
| | | | 424/78.27 |
| 2006/0079599 A1 | 4/2006 | Arthur | |
| 2008/0075657 A1 | 3/2008 | Abrahams et al. | |
| 2008/0281074 A1 | 11/2008 | Rozema | |
| 2008/0294089 A1 | 11/2008 | Hardy | |
| 2010/0016886 A1 | 1/2010 | Lu | |
| 2011/0123476 A1* | 5/2011 | Kapiamba | A61L 24/04 |
| | | | 424/78.06 |
| 2011/0224724 A1 | 9/2011 | Lu et al. | |
| 2012/0004194 A1 | 1/2012 | Lu et al. | |
| 2012/0027732 A1 | 2/2012 | Voytik-Harbin | |
| 2013/0060184 A1* | 3/2013 | Rea | A61F 13/0246 |
| | | | 602/54 |
| 2013/0136697 A1 | 5/2013 | Kannan et al. | |
| 2013/0195789 A1 | 8/2013 | Lu | |
| 2014/0235758 A1* | 8/2014 | Cheng | C09J 109/00 |
| | | | 523/438 |

FOREIGN PATENT DOCUMENTS

| | | |
|---|---|---|
| EP | 1 849 486 A1 | 10/2007 |
| FR | 2 872 822 A1 | 1/2006 |
| WO | 2008/151389 A1 | 12/2008 |
| WO | 2010070458 A2 | 6/2010 |
| WO | WO 2012142470 | * 10/2012 |

OTHER PUBLICATIONS

Scott et al. "Development of a Light-Deactivatable PSA via Photodimerization". Aug. 2004. WO 201242470.*
Serrero et al., "Polysaccharide-Based Adhesive for Biomedical Applications: Correlation Between Rheological Behavior and Adhesion," Biomacromolecules, 2011, 12(5):1556-1566.
Bhatia et al., "Polysaccharide-Based Tissue Adhesives for Sealing Corneal Incisions," Current Eye Research, 2007, 32(12):1045-50.
Majoros et al., "Poly(Amidoamine) Dendrimer-Based Multifunctional Engineered Nanodevice for Cancer Therapy," Journal of Medicinal Chemistry, 2005, 48(19):5892-5899.
Chen et al., "Cysteine and pH-Responsive Hydrogel Based on a Saccharide Derivative with an Aldehyde Group," Langmuir, 2009, 26(5):3165-3168.
Sannino et al., "Biodegradable Cellulose-Based Hydrogels: Design and Applications," Materials, 2009, 2:353-373.
Chen et al., "Polyethers Containing Coumarin Dimer Components in the Main Chain. II. Reversible Photocleavage and Photopolymerization," J. Appl. Polym. Sci., 1997, 64(9):1759-1768.
Chen et al., "Synthesis and Reversible Photocleavage of Novel Polyurethanes Containing Coumarin Dimer Components," J. Polym. Sci., Part A: Polym. Chem., 1997, 35:613-624.

(Continued)

*Primary Examiner* — Robert A Wax
*Assistant Examiner* — Danah Al-Awadi
(74) *Attorney, Agent, or Firm* — Eversheds Sutherland (US) LLP

(57) ABSTRACT

Methods for treating, adhering, or sealing biological tissue are provided. The methods include combining solutions containing a polymer component and a dendrimer component capable of reacting with each other, and at least one of the components includes a substituent capable of photoreversible dimerization that can be reversibly dimerized. Drug delivery compositions and kits containing these two components also are provided.

12 Claims, 6 Drawing Sheets

(56) References Cited

OTHER PUBLICATIONS

Jimenez et al., "Dextranase in Sugar Industry: A Review," Sugar Tech, 2007, 11(2):124-134.
Jung et al., "Drug Release from Core-Shell Type Nanoparticles of Poly(DL-lactide-co-glycolide)-Grated Dextran," J. of Microencapsulation, 2005, 22(8):901-911.
Kurisawa et al., "Double-Stimuli-Responsive Degradation of Hydrogels Consisting of Oligopeptide-Terminated Poly (ethylene glycol) and Dextran with an Interpenetrating Polymer Network," J. Biomater. Sci. Polymer, Ed., 1997, 8 (9):691-708.

* cited by examiner

US 9,877,984 B2

CONTROLLABLY DEGRADABLE COMPOSITIONS AND METHODS

CROSS-REFERENCE TO RELATED APPLICATION

This application claims priority to U.S. Provisional Patent Application No. 61/920,217, filed Dec. 23, 2013, which is incorporated herein by reference.

FIELD OF THE INVENTION

This disclosure relates to materials and adhesives capable of reversible dimerization, as well as methods and kits for making and using the materials and adhesives, including but not limited to biocompatible materials and adhesives, which may be particularly useful in medical, dental, and veterinary applications.

BACKGROUND

Crosslinking can be accomplished in a variety of ways, including chemically or by energy exposure, which can induce a conformational or internal chemical change in a material. Incorporation of photosensitive groups to a material allows on-demand polymerization with the application of ultraviolet (UV) light. Photosensitive polymers often are used in the fields of printing, inks, coatings, drug delivery, and tissue engineering. The photosensitive groups in the main or pendant chains of a polymer can polymerize or cleave after irradiation with UV light, depending on whether the groups are of a negative or positive type. This photosensitive capability can enhance the precision and control of the crosslinking of the material, whereas other types of polymerization cannot be controlled on demand. Conversely, polymers with o-nitrobenzyl moieties can efficiently transfer electrons upon UV irradiation, which results in the cleavage of the polymeric chains. However, none of these photosensitive materials is reversible, which forces a user to choose between the benefits of photopolymerization or photocleavage, exclusively.

One of the most appealing ways to control the application of materials to a specific site is by applying a material in a pre-state that can flow and integrate into irregular surfaces, increasing the surface area for interaction, and then crosslinking the material to fix it into place. Materials are desired that can reversibly crosslink on command.

There are several biocompatible adhesives that are commercially available. The commercially available adhesives, however, typically are difficult to remove. Healing and adhesion often create a powerful bond between the patient's tissues and the adhesive material, thereby preventing the removal of the adhesive material without disrupting the wound and potentially causing further injury. Therefore, first responders who need to control a wound immediately must decide whether applying the currently available adhesive materials is optimal for long term treatment.

It would be advantageous to have an adhesive or material that can stabilize a wound or serve another purpose, such as drug delivery, and prevent further injury while allowing health care providers to later selectively remove the material, for example, to permit further treatment, or to later activate the material to control drug release.

BRIEF SUMMARY OF THE INVENTION

Methods are provided for treating, adhering, or sealing biological tissues. In embodiments, the methods comprise providing a first solution comprising a polymer component, wherein the polymer component comprises a polymer having three or more aldehyde groups; providing a second solution comprising a dendrimer component, wherein the dendrimer component comprises a dendrimer having at least 2 branches with one or more surface groups; wherein at least one of the polymer and dendrimer is substituted with one or more substituents capable of photoreversible dimerization; combining the first and second solutions together to produce an adhesive formulation and contacting one or more biological tissues with the adhesive formulation; allowing the adhesive formulation to cure in contact with the one or more biological tissues; and contacting the adhesive formulation with light having a wavelength sufficient to dimerize the substituent capable of photoreversible dimerization.

Also provided are kits for making an adhesive or drug delivery composition. In embodiments, the kits comprise a first part which includes a first solution comprising a polymer component, wherein the polymer component comprises a polymer; and a second part which includes a second solution comprising a dendrimer component, wherein the dendrimer component comprises a dendrimer having at least 2 branches with one or more surface groups; wherein at least one of the polymer and dendrimer is substituted with one or more substituents capable of photoreversible dimerization.

Also provided are drug delivery compositions. In embodiments, the drug delivery compositions comprise a polymer component, wherein the polymer component comprises a polymer having three or more aldehyde groups; a dendrimer component, wherein the dendrimer component comprises a dendrimer having at least 2 branches with one or more surface groups; and at least one drug combined with the at least one of the polymer component and dendrimer component; wherein at least one of the polymer and dendrimer is substituted with one or more substituents capable of photoreversible dimerization.

DETAILED DESCRIPTION

Figure 1:
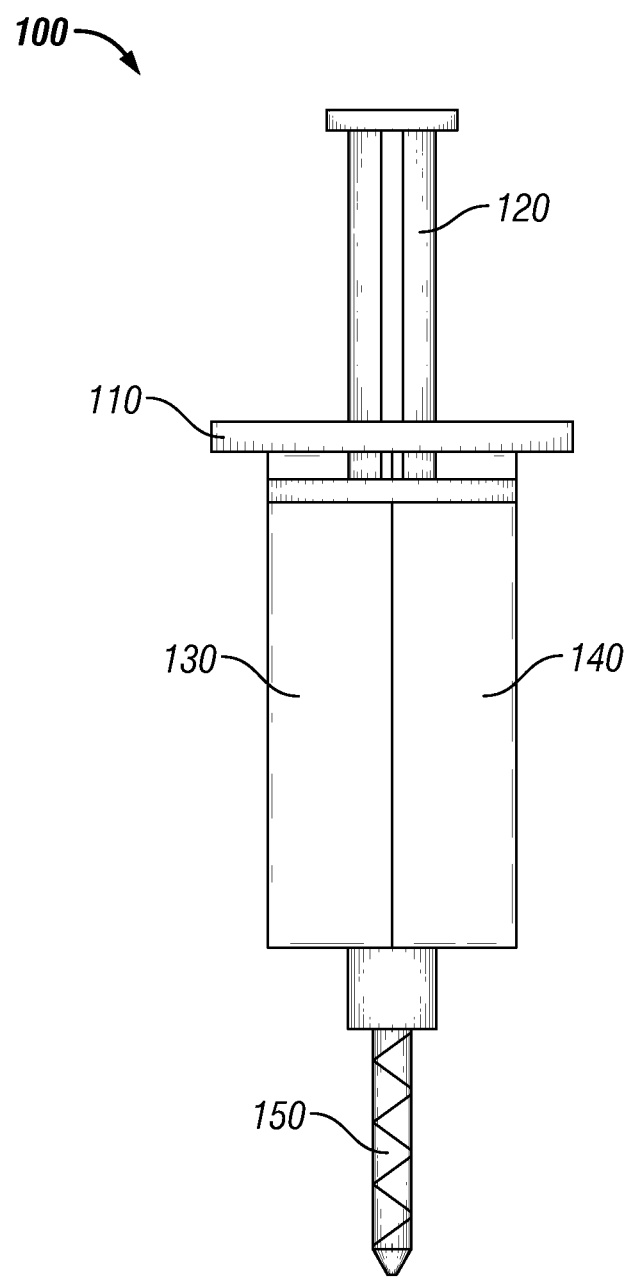
FIG. 1 depicts one embodiment of a kit containing the components of an adhesive formulation.

Provided herein are materials and adhesives that can be reversibly dimerized and methods of use thereof. In one embodiment, the materials and adhesives are reversibly crosslinkable. The materials and adhesives provided herein, in some embodiments, comprise one or more substituents capable of photoreversible dimerization. The substituents capable of photoreversible dimerization can form a dimer upon the application of one wavelength of light, and the dimer can be cleaved upon the application of a second wavelength of light. Therefore, the substituents capable of photoreversible dimerization can be bonded to each other upon the application of light, thereby crosslinking the materials or adhesives, or bonding together two molecules of the materials or adhesives. Upon the application of a different wavelength of light, the dimer can be cleaved, thereby reversing the crosslinking of the materials or adhesives, or severing the bond between two molecules of the materials or adhesives. The ability to remove the adhesives or materials rapidly advantageously can reduce additional injury associated with the removal of the adhesives or materials for additional medical treatment.

Generally, the materials and adhesives may be used on or in any amine-containing surface or area. For example, the materials and adhesives may be used on or in any internal or external biological tissues, lumens, orifices, or cavities. The biological tissues, lumens, orifices, or cavities may be human or other mammalian tissues, lumens, orifices, or cavities. The biological tissues may be natural or artificially generated. Therefore, the biological tissues may be in vivo or in vitro. The biological tissues may be skin, bone, ocular, muscular, vascular, or an internal organ, such as lung, intestine, heart, liver, etc.

In some embodiments, the materials or adhesives serve as a matrix material for controlled release of drug. In other embodiments, the materials or adhesives may be used in medical applications as a scaffold, filler, prosthetic, artificial tissue, or a combination thereof. The adhesives and materials can be applied to a tissue site in a human or other animal patient, for example, during a surgical or other medical procedure. In one embodiment, the adhesives are used to create an anastomosis. In particular embodiments, the adhesives or materials are used to adhere, seal, and/or treat a wound, lesion, or a combination thereof. For example, the adhesives or materials may be applied to slow-healing or troublesome wounds, such as those suffered by diabetics. In one embodiment, the materials or adhesives may be used to secure or help secure a medical implant, such as an orthopedic implant, within a human or other animal patient.

Biocompatible Adhesives

Improved compositions and methods have been developed for adhering, sealing, or treating one or more biological tissues. In one embodiment, these adhesive formulations include a dendrimer component and a polymer component. In some embodiments, the adhesive formulations are used as tissue adhesives, tissue sealants, tissue treatments, matrix materials, fillers, coatings, or a combination thereof.

As used herein, the term "adhering" generally refers to affixing, permanently or temporarily, two or more biological tissues, or two or more regions of a biological tissue. As used herein, the term "sealing" generally refers to covering, at least partially, or filling, at least partially, one or more sites on one or more biological tissues, such as a wound. As used herein, the term "treating" generally refers to improving the response of at least one biological tissue to which one or more adhesive formulations is applied. In some embodiments, the "response" that is improved or enhanced includes inflammation, healing, or both.

Generally, the biocompatible adhesives provided herein include an adhesive formulation comprising a dendrimer component and a polymer component. In one embodiment, the polymer component and the dendrimer component both include at least one substituent capable of photoreversible dimerization. In another embodiment, only the polymer component comprises at least one substituent capable of photoreversible dimerization. In yet another embodiment, only the dendrimer component comprises at least one substituent capable of photoreversible dimerization. In a still further embodiment, the polymer component and the dendrimer component do not comprise a substituent capable of photoreversible dimerization, but, in this embodiment, the crosslinking of the adhesives is controlled by one of the other methods provided herein.

Dendrimer Component

In embodiments, the dendrimer component comprises a dendrimer having amines on at least a portion of its surface groups, which are commonly referred to as "terminal groups" or "end groups." The dendrimer may have amines on from 20% to 100% of its surface groups. In some embodiments, the dendrimer has amines on 100% of its surface groups. In one embodiment, the dendrimer component comprises a dendrimer having amines on less than 75% of its surface groups. As used herein, the term "dendrimer" refers to any compound with a polyvalent core covalently bonded to two or more dendritic branches. In some embodiments, the polyvalent core is covalently bonded to three or more dendritic branches. In one embodiment, the amines are primary amines. In another embodiment, the amines are secondary amines. In yet another embodiment, one or more surface groups have at least one primary and at least one secondary amine.

In particular embodiments, at least a portion of the surface groups of the dendrimer comprise at least one substituent capable of photoreversible dimerization. The at least one substituent capable of photoreversible dimerization can be bonded to any functional group that is present in the surface groups. For example, in some embodiments, the at least one substituent capable of photoreversible dimerization may be bonded to a hydroxyl group of the surface group. In one embodiment, from about 10% to about 50% of the surface groups comprise at least one substituent capable of photoreversible dimerization. In another embodiment, from about 20% to about 40% of the surface groups comprise at least one substituent capable of photoreversible dimerization.

In some embodiments, at least a portion of the amines on the surface groups of the dendrimer are substituted with a substituent capable of photoreversible dimerization. As explained herein, the amines, due to their nucleophilicity, can be reacted, in particular embodiments, with a substituent capable of photoreversible dimerization. In one embodiment, from about 5% to about 75% of the amines are substituted with a substituent capable of photoreversible dimerization. In another embodiment, from about 10% to about 50% of the amines are substituted with a substituent capable of photoreversible dimerization. In yet another embodiment, from about 20% to about 40% of the amines are substituted with a substituent capable of photoreversible dimerization.

In one embodiment, the dendrimer extends through at least 2 generations. In another embodiment, the dendrimer extends through at least 3 generations. In yet another embodiment, the dendrimer extends through at least 4 generations. In still another embodiment, the dendrimer extends through at least 5 generations. In a further embodiment, the dendrimer extends through at least 6 generations. In still a further embodiment, the dendrimer extends through at least 7 generations.

In one embodiment, the dendrimer has a molecular weight of from about 1,000 to about 1,000,000 Daltons. In a further embodiment, the dendrimer has a molecular weight of from about 3,000 to about 120,000 Daltons. In another embodiment, the dendrimer has a molecular weight of from about 10,000 to about 100,000 Daltons. In yet another embodiment, the dendrimer has a molecular weight of from about 20,000 to about 40,000 Daltons. Unless specified otherwise, the "molecular weight" of the dendrimer refers to the number average molecular weight.

Generally, the dendrimer may be made using any known methods. In one embodiment, the dendrimer is made by oxidizing a starting dendrimer having surface groups comprising at least one hydroxyl group so that at least a portion of the surface groups comprise at least one amine. In another embodiment, the dendrimer is made by oxidizing a starting generation 5 (G5) dendrimer having surface groups comprising at least one hydroxyl group so that at least a portion of the surface groups comprise at least one amine. In yet another embodiment, the dendrimer is made by oxidizing a starting G5 dendrimer having surface groups comprising at least one hydroxyl group so that about 25% of the surface groups comprise at least one amine. In a particular embodiment, the dendrimer is a G5 dendrimer having primary amines on about 25% of the dedrimer's surface groups.

In one embodiment, the dendrimer is a poly(amidoamine)-derived (PAMAM) dendrimer. In another embodiment, the dendrimer is a G5 PAMAM-derived dendrimer. In yet another embodiment, the dendrimer is a G5 PAMAM-derived dendrimer having primary amines on about 25% of the dendrimer's surface groups.

In one embodiment, the dendrimer is a poly(propyleneimine)-derived dendrimer.

In certain embodiments, the dendrimer component is combined with a liquid to form a dendrimer component solution. In one embodiment, the dendrimer component solution is an aqueous solution. In one embodiment, the solution comprises water, phosphate buffer saline (PBS), Dulbecco's Modified Eagle's Medium (DMEM), or any combination thereof. In one embodiment, the dendrimer component concentration in the dendrimer component solution is about 5% to about 25% by weight. In another embodiment, the dendrimer component concentration in the dendrimer component solution is about 10% to about 20% by weight. In a further embodiment, the dendrimer component concentration in the dendrimer component solution is about 11% to about 15% by weight.

In some instances, the dendrimer component or dendrimer component solution further includes one or more additives. Generally, the amount of additive may vary depending on the application, tissue type, concentration of the dendrimer component solution, the type of dendrimer component, concentration of the polymer component solutions, and/or the type of polymer component. Example of suitable additives, include but are not limited to, pH modifiers, thickeners, antimicrobial agents, colorants, surfactants, and radio-opaque compounds. Specific examples of these types of additives are described herein. In one embodiment, the dendrimer component solution comprises a foaming additive.

In particular embodiments, the dendrimer component or dendrimer component solution includes one or more drugs. In such embodiments, the adhesive formulation may serve as a matrix material for controlled release of the one or more drugs. The drug may be essentially any drug suitable for local, regional, or systemic administration from a quantity of the adhesive formulation that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicyclic acid acetate, ibuprophen, sulindac, piroxicam, naproxen, and combinations thereof. In still another embodiment, the drug comprises an anti-neoplastic agent. In still other embodiments, the drug is one for gene therapy. For example, the drug may comprise siRNA molecules to combat cancer. Other drugs are envisioned.

In other particular embodiments, the dendrimer component or dendrimer component solution includes one or more cells. Alternatively or in addition, the polymer component or polymer component solution includes one or more cells. For example, in any of these embodiments, the adhesive formulation may serve as a matrix material for delivering cells to a tissue site at which the adhesive formulation has been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Polymer Component

Generally, the polymer component includes a polymer and/or oligomer with one or more functional groups capable of reacting with one or more functional groups on a biological tissue and/or one or more functional groups on the dendrimer component.

In some embodiments, the polymer of the polymer component is substituted with at least one group capable of photoreversible dimerization.

In certain embodiments, the polymer is at least one polysaccharide. In these embodiments, the at least one polysaccharide may be linear, branched, or have both linear and branched sections within its structure. Generally, the at least one polysaccharide may be natural, synthetic, or modified—for example, by cross-linking, altering the polysaccharide's substituents, or both. In one embodiment, the at least one polysaccharide is plant-based. In another embodiment, the at least one polysaccharide is animal-based. In yet another embodiment, the at least one polysaccharide is a combination of plant-based and animal-based polysaccharides. Non-limiting examples of polysaccharides include, but are not limited to, dextran, chitin, starch, agar, cellulose, hyaluronic acid, or a combination thereof.

In certain embodiments, the at least one polymer has a molecular weight of from about 1,000 to about 1,000,000

Daltons. In one embodiment, the at least one polymer has a molecular weight of from about 5,000 to about 15,000 Daltons. Unless specified otherwise, the "molecular weight" of the polymer refers to the number average molecular weight.

In some embodiments, the polymer is functionalized so that its structure includes one or more functional groups that will react with one or more functional groups on a biological tissue and/or one or more functional groups on the dendrimer component. In other embodiments, the polymer is functionalized so that its structure includes three or more functional groups that will react with one or more functional groups on a biological tissue and/or one or more functional groups on the dendrimer component. In one embodiment, the functional groups incorporated into the polymer's structure is aldehyde.

In certain embodiments, the polymer's degree of functionalization is adjustable. The "degree of functionalization" generally refers to the number or percentage of groups on the polymer that are replaced or converted to the desired one or more functional groups. The one or more functional groups, in particular embodiments, include aldehydes, substituents capable of photoreversible dimerization, or a combination thereof. In one embodiment, the degree of functionalization is adjusted based on the type of tissue to which the adhesive is applied, the concentration(s) of the components, and/or the type of polymer or dendrimer used in the adhesive. In one embodiment, the degree of functionalization is from about 10% to about 75%. In another embodiment, the degree of functionalization is from about 15% to about 50%. In yet another embodiment, the degree of functionalization is from about 20% to about 30%.

In one embodiment, the polymer is a polysaccharide having from about 10% to about 75% of its hydroxyl groups converted to aldehydes, substituents capable of photoreversible dimerization, or a combination thereof. In another embodiment, the polymer is a polysaccharide having from about 20% to about 50% of its hydroxyl groups converted to aldehydes, substituents capable of photoreversible dimerization, or a combination thereof. In yet another embodiment, the polymer is a polysaccharide having from about 10% to about 30% of its hydroxyl groups converted to aldehydes, and from about 10% to about 30% of its hydroxyl groups converted to substituents capable of photoreversible dimerization.

In one embodiment, the polymer is dextran with a molecular weight of about 10 kDa. In another embodiment, the polymer is dextran having about 50% of its hydroxyl group converted to aldehydes, substituents capable of photoreversible dimerization, or a combination thereof. In a further embodiment, the polymer is dextran with a molecular weight of about 10 kDa and about 50% of its hydroxyl groups converted to aldehydes, substituents capable of photoreversible dimerization, or a combination thereof.

In some embodiments, a polysaccharide is oxidized to include a desired percentage of one or more aldehyde functional groups. Generally, this oxidation may be conducted using any known means. For example, suitable oxidizing agents include, but are not limited to, periodates, hypochlorites, ozone, peroxides, hydroperoxides, persulfates, and percarbonates. In one embodiment, the oxidation is performed using sodium periodate. Typically, different amounts of oxidizing agents may be used to alter the degree of functionalization.

In certain embodiments, the polymer component is combined with a liquid to form a polymer component solution. In one embodiment, the polymer component solution is an aqueous solution. In one embodiment, the solution comprises water, PBS, DMEM, or any combination thereof.

Generally, the polymer component solution may have any suitable concentration of polymer component. In one embodiment, the polymer component concentration in the polymer component solution is about 5% to about 40% by weight. In another embodiment, the polymer component concentration in the polymer component solution is about 5% to about 30% by weight. In yet another embodiment, the polymer component concentration in the polymer component solution is about 5% to about 25% by weight. Typically, the concentration may be tailored and/or adjusted based on the particular application, tissue type, and/or the type and concentration of dendrimer component used.

The polymer component or polymer component solution may also include one or more additives. In one embodiment, the additive is compatible with the polymer component. In another embodiment, the additive does not contain primary or secondary amines. Generally, the amount of additive varies depending on the application, tissue type, concentration of the polymer component solution, the type of polymer component and/or dendrimer component. Examples of suitable additives, include, but are not limited to, pH modifiers, thickeners, antimicrobial agents, colorants, surfactants, radio-opaque compounds, and the other additives described herein. In other embodiments, the polymer component solution comprises a foaming agent.

In certain embodiments, the pH modifier is an acidic compound. Examples of acidic pH modifiers include, but are not limited to, carboxylic acids, inorganic acids, and sulfonic acids. In other embodiments, the pH modifier is a basic compound. Examples of basic pH modifiers include, but are not limited to, hydroxides, alkoxides, nitrogen-containing compounds other than primary and secondary amines, basic carbonates, and basic phosphates.

Generally, the thickener may be selected from any known viscosity-modifying compounds, including, but not limited to, polysaccharides and derivatives thereof, such as starch or hydroxyethyl cellulose.

Generally, the surfactant may be any compound that lowers the surface tension of water. In one embodiment, the surfactant is an ionic surfactant—for example, sodium lauryl sulfate. In another embodiment, the surfactant is a neutral surfactant. Examples of neutral surfactants include, but are not limited to, polyoxyethylene ethers, polyoxyethylene esters, and polyoxyethylene sorbitan.

In one embodiment, the radio-opaque compound is barium sulfate, gold particles, or a combination thereof.

In particular embodiments, the polymer component or polymer component solution includes one or more drugs. In such embodiments, the adhesive formulation may serve as a matrix material for controlled release of drug. The drug may be essentially any drug suitable for local, regional, or systemic administration from a quantity of the adhesive formulation that has been applied to one or more tissue sites in a patient. In one embodiment, the drug comprises a thrombogenic agent. Non-limiting examples of thrombogenic agents include thrombin, fibrinogen, homocysteine, estramustine, and combinations thereof. In another embodiment, the drug comprises an anti-inflammatory agent. Non-limiting examples of anti-inflammatory agents include indomethacin, salicyclic acid acetate, ibuprophen, sulindac, piroxicam, naproxen, and combinations thereof. In still another embodiment, the drug comprises an anti-neoplastic agent. In still other embodiments, the drug is one for gene or cell therapy. For example, the drug may comprise siRNA molecules to combat cancer. Other drugs are envisioned.

In other particular embodiments, the polymer component or polymer component solution includes one or more cells. For example, the adhesive formulation may serve as a matrix material for delivering cells to a tissue site at which the adhesive formulation has been applied. In embodiments, the cells may comprise endothelial cells (EC), endothelial progenitor cells (EPC), hematopoietic stem cells, or other stem cells. In one embodiment, the cells are capable of releasing factors to treat cardiovascular disease and/or to reduce restenosis. Other types of cells are envisioned.

Adhesive Formulation

Generally, the adhesive formulations described herein may be formed by combining the polymer component or polymer component solution, and the dendrimer component or dendrimer component solution in any manner. In some embodiments, the polymer component or polymer component solution, and the dendrimer component or dendrimer component solution are combined before contacting a biological tissue with the adhesive formulation. In other embodiments, the polymer component or polymer component solution, and the dendrimer component or dendrimer component solution are combined, in any order, on a biological tissue. In further embodiments, the polymer component or polymer component solution is applied to a first biological tissue, the dendrimer component or dendrimer component solution is applied to a second biological tissue, and the first and second biological tissues are contacted. In still a further embodiment, the polymer component or polymer component solution is applied to a first region a biological tissue, the dendrimer component or dendrimer component solution is applied to a second region of a biological tissue, and the first and second regions are contacted.

Generally, the substituents capable of photoreversible dimerization may be activated or deactivated at any time. As used herein, the "activated" refers to dimerizing the substituents capable of photoreversible dimerization. As used herein, "deactivated" refers to cleaving the dimer formed when the substituents capable of photoreversible dimerization are dimerized. In some embodiments, the polymer component or polymer component solution, and the dendrimer component or dendrimer component solution are combined before contacting a biological tissue with the adhesive formulation, and the substituents capable of photoreversible dimerization are activated after contacting the biological tissue with the adhesive formulation. In other embodiments, the polymer component or polymer component solution, and the dendrimer component or dendrimer component solution are combined, in any order, on a biological tissue followed by activation of the substituents capable of photoreversible dimerization. In further embodiments, the polymer component or polymer component solution is applied to a first biological tissue, the dendrimer component or dendrimer component solution is applied to a second biological tissue, and the first and second biological tissues are contacted, and then the substituents capable of photoreversible dimerization are activated. In still a further embodiment, the polymer component or polymer component solution is applied to a first region a biological tissue, the dendrimer component or dendrimer component solution is applied to a second region of a biological tissue, and the first and second regions are contacted, and then the substituents capable of photoreversible dimerization are activated. Once activated, the substituents capable of photoreversible dimerization may be deactivated at any time.

Generally, the adhesive formulation may be applied to one or more biological tissues as an adhesive, sealant, and/or treatment. The one or more biological tissues may be diseased, damaged (e.g., dissected), healthy, or some combination thereof. In one embodiment, the adhesive formulation is applied to one or more biological tissues as an adhesive. In another embodiment, the adhesive formulation is applied to one or more biological tissues as a sealant. In a further embodiment, the adhesive formulation is applied to one or more biological tissues as a treatment. In an additional embodiment, the adhesive formulation is applied to one or more biological tissues as an adhesive and sealant. In still another embodiment, the adhesive formulation is applied to one or more biological tissues as an adhesive and treatment. In yet another embodiment, the adhesive formulation is applied to one or more biological tissues as a sealant and treatment. In a still further embodiment, the adhesive formulation is applied to one or more biological tissues as an adhesive, sealant, and treatment.

The adhesive formation may be applied to the biological tissue using any suitable tool and methods. Non-limiting examples include the use of syringes or spatulas. Double barrel syringes with rigid or flexible discharge tips, and optional extension tubes, known in the art are envisioned.

As used herein, the adhesive formulation is a "treatment" when it improves the response of at least one biological tissue to which it is applied. In some embodiments, the improved response is lessening overall inflammation, improving the specific response at the wound site/interface of the tissue and adhesive formulation, enhancing healing, or a combination thereof. As used herein, the phrase "lessening overall inflammation" refers to an improvement of histology scores that reflect the severity of inflammation. As used herein, the phrase "improving the specific response at the wound site/interface of the tissue and adhesive formulation" refers to an improvement of histology scores that reflect the severity of serosal neutrophils. As used herein, the phrase "enhancing healing" refers to an improvement of histology scores that reflect the severity of serosal fibrosis.

After contacting one or more biological tissues, the adhesive formulations may be allowed adequate time to cure or gel. When the adhesive formulation "cures" or "gels," as those terms are used herein, it means that the reactive groups (other than the substituents capable of photoreversible dimerization) on the polymer component, dendrimer component, and one or more biological tissues have undergone one or more reactions. Not wishing to be bound by any particular theory, it is believed that the adhesive formulations described herein are effective because the polymer component reacts with both the dendrimer component and the surface of the biological tissues. In certain embodiments, the polymer component's aldehyde functional groups react with the amines on the dendrimer component and the biological tissues to form imine bonds. In these embodiments, it is believed that the amines on the dendrimer component react with a high percentage of the aldehydes on the polymer component, thereby reducing toxicity and increasing biocompatibility of the adhesive formulations. Typically, the time needed to cure or gel the adhesive formulations will vary based on a number of factors, including, but not limited to, the characteristics of the polymer component and/or dendrimer component, the concentrations of the polymer component solution and/or the dendrimer component solution, and the characteristics of the one or more biological tissues. In embodiments, the adhesive formulation will cure sufficiently to provide desired bonding or sealing shortly after the components are combined. The gelation or cure time should provide that a mixture of the components can be delivered in fluid form to a target area before becoming too viscous or solidified and then once applied to the target area sets up rapidly thereafter. In one embodiment, the gelation or cure time is less than 120 seconds. In another embodiment, the gelation or cure time is between 3 and 60 seconds. In a particular embodiment, the gelation or cure time is between 5 and 30 seconds. Before or after the adhesive formulation has cured, the substituents capable of photoreversible dimerization may be activated or deactivated as desired.

In certain embodiments, one or more foaming agents are added to the polymer component solution and/or the dendrimer component solution before the solutions are combined. In one embodiment, the foaming agents comprise a two part liquid system comprising Part 1 and Part 2, wherein Part 1 comprises a bicarbonate and Part 2 comprises an aqueous solution of di- or polyaldehydes and a titrant. A wide range of di- or polyaldhydes exist, and their usefulness is restricted largely by availability and by their solubility in water. For example, aqueous glyoxal (ethanedial) is useful, as is aqueous glutaraldehyde (pentadial). Water soluble mixtures of di- and polyaldehydes prepared by oxidative cleavage of appropriate carbohydrates with periodate, ozone or the like may also be useful.

A titrant is most preferably employed in the liquid solution of Part 2. More specifically, the titrant is an organic or inorganic acid, buffer, salt, or salt solution which is capable of reacting with the bicarbonate component of Part 1 to generate carbon dioxide and water as reaction by-products. The carbon dioxide gas that is generated creates a foam-like structure of the adhesive formulation and also causes the volume of the adhesive formulation to expand.

Most preferably, the titrant is an inorganic or organic acid that is present in an amount to impart an acidic pH to the resulting mixture of the Part 1 and Part 2 components. Preferred acids that may be employed in the practice of the present invention include phosphoric acid, sulfuric acid, hydrochloric acid, acetic acid, and citric acid.

Tissue Specific Formulations

The adhesives provided herein, in some embodiments, are capable of binding specifically to individual tissue elements and allowing directed and on-demand reversible adhesion.

Generally, the polymer component and the dendrimer component that are combined to form the adhesive formulation may be tailored for specific biological tissues. For example, the type of components or the amounts of one or both of the components may be adjusted. Not wishing to be bound by any particular theory, it is believed that performing an analysis to determine the density of amine groups on the surface of a biological tissue may guide the determination of how to alter the adhesive formulations. In one embodiment, aldehyde-coated fluorescent microspheres (f-MS) are applied to various tissues to aid this analysis.

Generally, the adhesive formulations may be adjusted in any manner to compensate for differences between tissues. In one embodiment, the amount of polymer component is increased or decreased while the amount of dendrimer component is unchanged. In another embodiment, the amount of dendrimer component is increased or decreased while the amount of polymer component is unchanged. In another embodiment, the concentration of the polymer component solution is increased or decreased while the dendrimer component or dendrimer component solution is unchanged. In yet another embodiment, the concentration of the dendrimer component solution is increased or decreased while the polymer component or polymer component solution is unchanged. In a further embodiment, the concentrations of the both the polymer component solution and the dendrimer component solution are changed.

When the amine density on the surface of a particular biological tissue is unknown due to disease, injury, or otherwise, an excess of polymer component or polymer component solution may, in some embodiments, be added when the adhesive formulation is first applied, then the amount of polymer component or polymer component solution may be reduced, e.g., incrementally or drastically, until the desired effect is achieved. The "desired effect," in this embodiment, may be an appropriate or adequate curing time, adhesion, sealing, or a combination thereof. Not wishing to be bound by any particular theory, it is believed that an excess of polymer component or polymer component solution may be required, in some instances, to obtain the desired effect when the amine density on a biological tissue is low. Therefore, adding an excess will help the user, in this embodiment, achieve adequate sealing or adhesion in less time. This is particularly desirable in emergency situations.

In other embodiments, however, a lower amount of polymer component or polymer component solution may be added when the adhesive formulation is first applied, then the amount of polymer component or polymer component solution may be increased, e.g., incrementally or drastically, until the desired effect is achieved, which may be adequate curing time, adhesion, sealing, or a combination thereof.

Adhesive Formulation Kits

In another aspect, a kit is provided that comprises a first part that includes a polymer component or polymer component solution, and a second part that includes a dendrimer component or dendrimer component solution. The kit may further include an applicator or other device means, such as a multi-compartment syringe, for storing, combining, and delivering the two parts and/or the resulting adhesive formulation to a tissue site. The kit may also include a light source, including a UV light source, that may be used to activate/deactivate the substituents capable of photoreversible dimerization.

In one embodiment, the kit comprises separate reservoirs for the polymer component solution and the dendrimer component solution. In certain embodiments, the kit comprises reservoirs for polymer component solutions of different concentrations. In other embodiments, the kit comprises reservoirs for dendrimer component solutions of different concentrations.

In one embodiment, the kit comprises instructions for selecting an appropriate concentration or amount of at least one of the polymer component, polymer component solution, dendrimer component, or dendrimer component solution to compensate or account for at least one characteristic of one or more biological tissues. In one embodiment, the adhesive formulation is selected based on one or more predetermined tissue characteristics. For example, previous tests, such as those described herein, may be performed to determine the number of density of bonding groups on a biological tissue in both healthy and diseased states. Alternatively, a rapid tissue test may be performed to assess the number or density of bonding groups. Quantification of tissue bonding groups can be performed by contacting a tissue with one or more materials that (1) have at least one functional group that specifically interacts with the bonding groups, and (2) can be assessed by way of fluorescence or detachment force required to separate the bonding groups and the material. In another embodiment, when the density of bonding groups on a biological tissue is unknown, an excess of the polymer component, such as one containing aldehydes, may be initially added as described herein to gauge the density of bonding groups on the surface of the biological tissue.

In certain embodiments, the kit comprises at least one syringe. In one embodiment, the syringe comprises separate reservoirs for the polymer component solution and the dendrimer component solution. The syringe may also comprise a mixing tip that combines the two solutions as the plunger is depressed. The mixing tip may be releasably securable to the syringe (to enable exchange of mixing tips), and the mixing tip may comprise a static mixer. In some embodiments, the reservoirs in the syringe may have different sizes or accommodate different volumes of solution. In other embodiments, the reservoirs in the syringe may be the same size or accommodate the same volumes of the solution. In a further embodiment, one reservoir may comprise Part 1 of the foaming composition described hereinabove, and a second reservoir may comprise Part 2 of the foaming composition.

FIG. 1 depicts one embodiment of a syringe 100. The syringe 100 includes a body 110 with two reservoirs (130, 140). A dendrimer component solution is disposed in the first reservoir 130, and a polymer component solution is disposed in the second reservoir 140. The two reservoirs (130, 140) are emptied by depressing the plunger 120, which pushes the contents of the two reservoirs (130, 140) into the mixing tip 150 and out of the syringe 100.

In a further embodiment, one or more of the reservoirs of the syringe may be removable. In this embodiment, the removable reservoir may be replaced with a reservoir containing a polymer component solution or a dendrimer component solution of a desired concentration.

In a preferred embodiment, the kit is sterile. For example, the components of the kit may be packaged together, for example in a tray, pouch, and/or box. The packaged kit may be sterilized using known techniques at suitable wavelengths (where applicable), such as electron beam irradiation, gamma irradiation, ethylene oxide sterilization, or other suitable techniques.

Reversibly Dimerizable Materials

Materials are provided that can be reversibly dimerized. The materials comprise one or more substituents that are capable of photoreversible dimerization. The material can be a polymer as described above and used in the adhesives (or a monomer or oligomer thereof). The material also can be a dendrimer as described above, however, the dendrimer does not need to include any surface groups containing amines. In one embodiment, the material comprises a polymer as described above and a dendrimer that does not include any surface groups containing amines.

When the reversibly dimerizable material is a polymer and the polymer is substituted with at least one substituent capable of photoreversible dimerization, activating the at least one substituent capable of photoreversible dimerization crosslinks the polymer.

The materials may include any additive or drug provided herein. When the materials are embedded with drugs, the materials can enable the on-demand release of the drug.

The materials also may be included in a kit along with the adhesive or independently.

Substituents Capable of Photoreversible Dimerization

Generally, the at least one substituent capable of photoreversible dimerization is a substituent that can be activated when exposed to a first wavelength of light, and deactivated when exposed to a second wavelength of light. In other words, the substituent capable of photoreversible dimerization is capable of forming a dimer when exposed to a first wavelength of light, and the dimer can be cleaved when exposed to a second wavelength of light. As used herein, the term "dimer" includes two substituents capable of photoreversible dimerization that have been bonded to each other due to the application of one wavelength of light. The dimers described herein may be formed by two substituents capable of photoreversible dimerization that have the same structures. Alternatively, in some embodiments, two substituents capable of photoreversible dimerization that form the dimer have different structures.

In one embodiment, the at least one substituent capable of photoreversible dimerization is coumarin. In another embodiment, the at least one substituent capable of photoreversible dimerization is a coumarin derivative. In some embodiments, the at least one substituent capable of photoreversible dimerization is 7-hydroxycoumarin.

In one embodiment, the substituent capable of photoreversible dimerization is methyl-substituted coumarin. It is believed that the use of methyl-substituted coumarin can enhance the photocleavage reaction as compared to non-methyl-substituted coumarin. There is evidence in the chemical literature indicating that the presence of a methyl substituent greatly enhances the reversibility of the coumarins (see Chen, Y., et al. J. APPL. POLYM. SCI. 1997, 64, 1759; Chen, Y., et al. J. POLYM. SCI., PART A: POLYM. CHEM. 1997, 35, 613; and Chen, Y., et al. J. APPL. POLYM. SCI. 1997, 64, 1749).

The substituents capable of photoreversible dimerization may be bonded to the materials and adhesives, or components thereof, using any methods known in the art. In embodiments in which the substituent capable of photoreversible dimerization is coumarin or a coumarin derivative, the coumarin or coumarin derivative may be substituted with a carboxylic acid, which can form an amide bond with the adhesives and materials, or components thereof, that contain amines. The carboxylic acid also may be converted to an acyl chloride, which may be reacted with the hydroxyl groups of the adhesives and materials, or components thereof, to bond the coumarin or coumarin derivatives to the adhesives and materials, or components thereof.

Other Additives and Substituents

In addition to the other additives described herein, the adhesives and materials provided herein also may be combined with or be bonded to other additives and substituents. The other additives and substituents provided herein may be used alone or in combination.

In some embodiments, the materials and adhesives provided herein also may be substituted with additional photosensitizers. The photosensitizers, in some embodiments, are used to reduce the time of irradiation needed to dimerize the substituent capable of photoreversible dimerization. In one embodiment, the additional photosensitizer is benzophenone. It is believed that benzophenone forces the equilibrium between syn and anti photodimers of coumarin to the latest isomer form. Favoring the anti photodimers seems to increase the coumarin dimerization rate without changing the photocleavage rate.

In some embodiments, the materials and adhesives provided herein may be contacted with one or more substances, typically following selective placement and/or use of such materials and adhesives, as an accompaniment to the reversal of the dimerization, in order to purposefully enhance or speed degradation/removal of the materials and adhesives. For example, it may be desirable to enhance removal of the adhesive applied by a first responder to a tissue wound in order to permit the subsequent access and treatment of the wound. As another example, it may be desirable to speed degradation of the material or adhesive to facilitate controlled release of a drug or cells contained therein. Other uses are envisioned.

In one embodiment the substance includes an enzyme. In certain embodiments, the enzyme is a substance that eases the removal of the material or adhesive, for example, by degrading one or more components of the materials or adhesives. The at least one enzyme may be applied to materials and adhesives that contain at least one substituent capable of photoreversible dimerization. Alternatively, the at least one enzyme may be applied to materials and adhesives that do not contain at least one substituent capable of photoreversible dimerization. In particular embodiments, the enzyme degrades a polymer of the materials and adhesives. In one embodiment, the enzyme degrades a polysaccharide polymer. In one particular embodiment, the enzyme is a dextranase that degrades dextran.

In another embodiment, the substance includes a pH modifier. In one case, the pH modifier is a solution that can be applied to the materials or adhesives. The pH modifier may speed the degradation of the materials or adhesives. For example, aqueous solutions of dextran are stable at a pH ranging from 4 to 10. Outside of this range, however, dextran undergoes rapid degradation. Therefore, the pH modifier may be used to lower or raise the pH so that it falls outside this range. It should be noted, however, that a dendrimer containing unprotonated surface amines has a high buffering capacity in acidic conditions. In basic conditions, however, such a dendrimer has lower buffering capability. Therefore, a pH modifier that lowers the pH of the dextran's environment may be better at speeding the dextran's degradation than a pH modifier that raises the pH of the dextran's environment.

In still another embodiment, the substance includes amines. In one case, amines are added to the materials or adhesives to speed their degradation. Amines may be used alone or in combination with the other additives provided herein. Amines may be applied to a material or adhesive comprising at least one substituent capable of photoreversible dimerization. Alternatively, amines may be applied to a material or adhesive that does not comprise at least one substituent capable of photoreversible dimerization. The amines are especially effective at degrading the adhesives containing a polymer component and a dendrimer component that react to form imine bonds. Although imine bonds are reversibly formed, the imine bond is thermodynamically and kinetically favored. When different types of amines are present in a material or adhesive with aldehydes, however, the different types of amines compete to form imine bonds with the aldehydes. The amine that has the greatest affinity for the aldehydes will form imine bonds with greater frequency. If a strong amine nucleophile is added to a material that has already formed imine bonds with amines of moderately strong nucleophilic character, an exchange of amines if facilitate that will change the crosslinking structure. The change of the crosslinking structure may weaken or speed the degradation of the material or adhesive. In one embodiment, the amines comprise hydroxylamine.

In one embodiment, a pre-crosslinked dextran-dendrimer adhesive layer coupled to a solid backing layer could be applied to the wound. The adhesive would then crosslink with the amines of the tissue, sealing the injury and preventing any wound stretch, leaking, or infection. Once in the hospital, the tape may be sprayed with a hydroxylamine solution. The body-hydrogel adhesion, therefore, could be diminished and the tape could be quickly removed with any additional injury, as opposed to the current medical tapes in the market.

It is believed that the adhesives provided herein can be applied rapidly to a wound, allow for control of hemostasis, induce healing, protect against infection and further injury, or a combination thereof, while at the same time permitting removal of the adhesive without additional injury.

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

EXAMPLES

Example 1—Reversible Adhesive

A biocompatible adhesive containing two-components was designed and optimized. The two components included dextran substituted with aldehyde groups and a dendrimer containing amines on a portion of its surface groups. The two components also were substituted with photosensitive coumarin substituents, which were capable of being photoreversibly dimerized.

The two components of this particular example interacted with tissue to provide a cohesive gel through aldehyde-amine cross-linking, as shown by the following scheme.

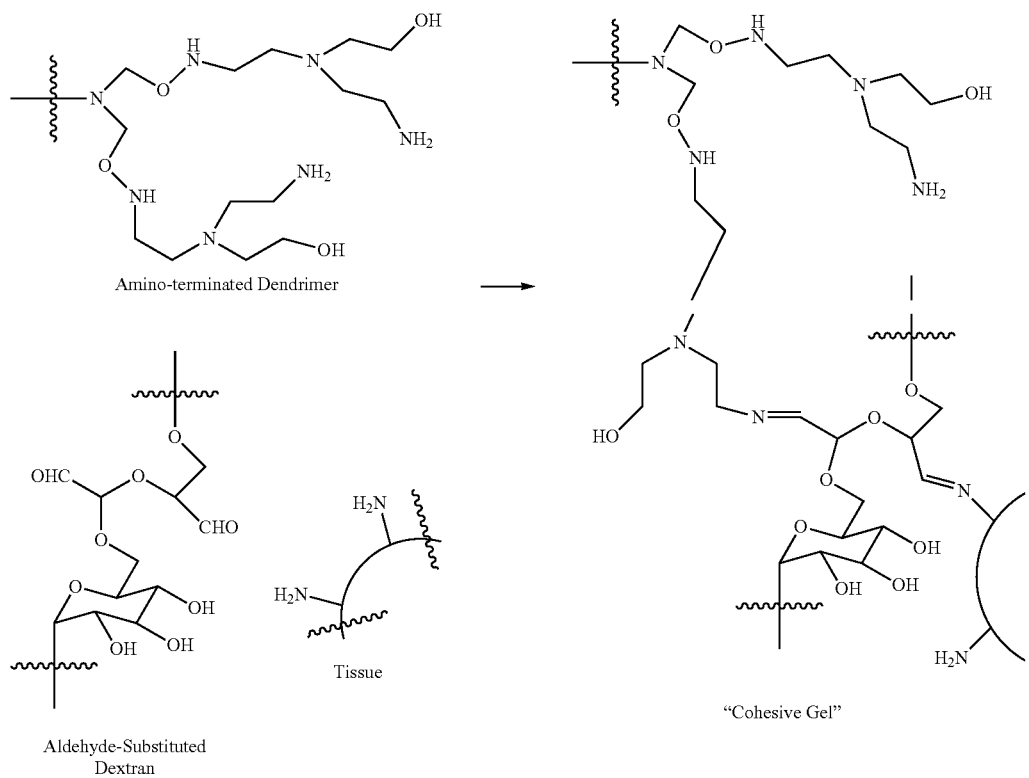

Scheme 1 - Formation of cohesive hydrogel.

The two components also allowed the crosslinking density to be modified due to the substitution of a portion of the aldehydes and amines of the dextran and dendrimer components, respectively, with photosensitive coumarins. In response to different wavelengths of UV light, the photosensitive coumarins react as shown in the following scheme.

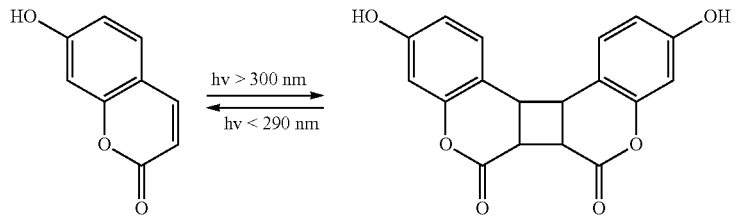

Scheme 2 - Reversibility of coumarin substituent.

The photosensitive coumarins were able to dimerize reversibly on-demand upon irradiation with different wavelengths of light. Exposure of the coumarin to UV light at 300 nm destabilized the distribution of electrons and stimulated the dimerization between two of the coumarin substituents, while irradiation at 254 nm cleaved the bonds forming the dimers and reverted the coumarin substituents to their original monomeric structures.

The reaction between the amines of the dendrimer and the aldehydes of the dextran caused rapid gel formation, while the coumarin substituents allowed for on demand degradation and crosslinking, which permitted fast removal of the material, as shown in the following scheme.

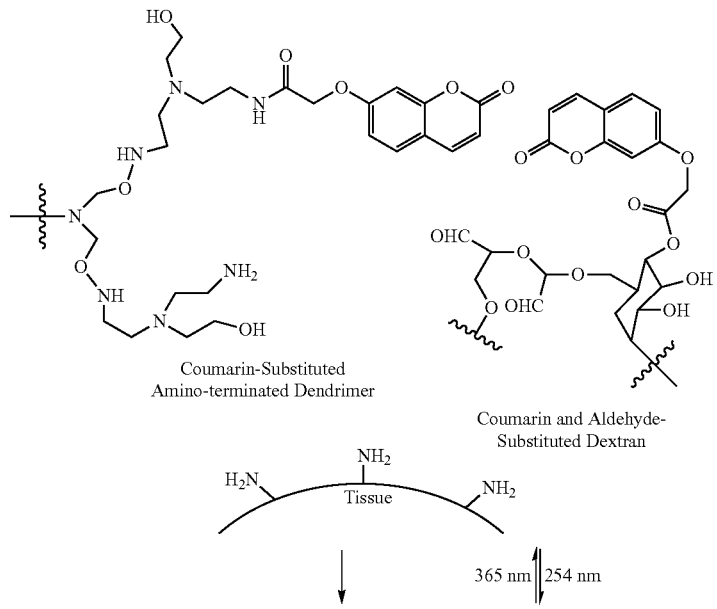

Scheme 3 - Reversibility of Substituents Derived from Coumarin

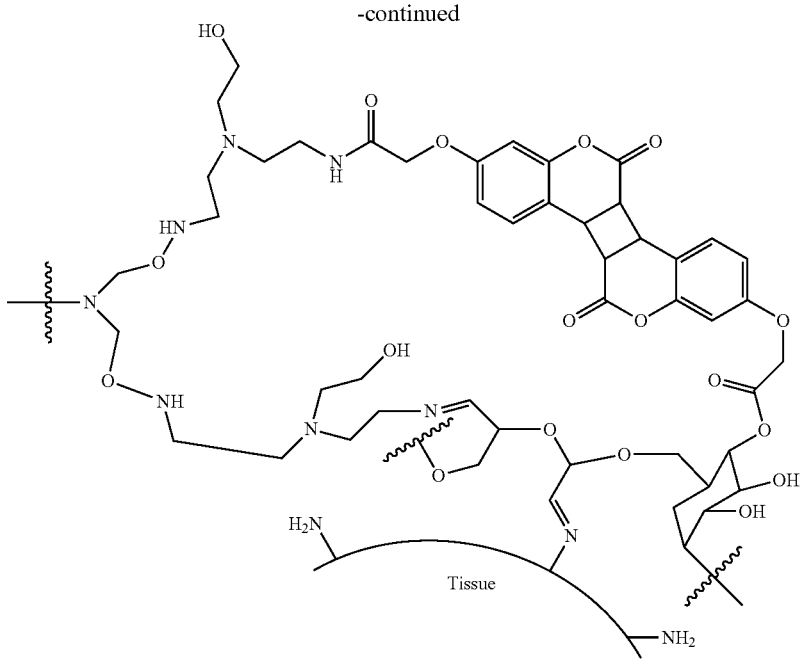

The components can be substituted with the coumarins in a variety of ways. In this example, the coumarin used was 7-hydroxycoumarin, which was reacted with the amines of the dendrimer or with the hydroxyl groups present on both the dendrimer and the dextran component.

To substitute the amines of the dendrimer with 7-hydroxycoumarin, the 7-hydroxycoumarin was first substituted with a carboxylic acid, as shown in the following scheme.

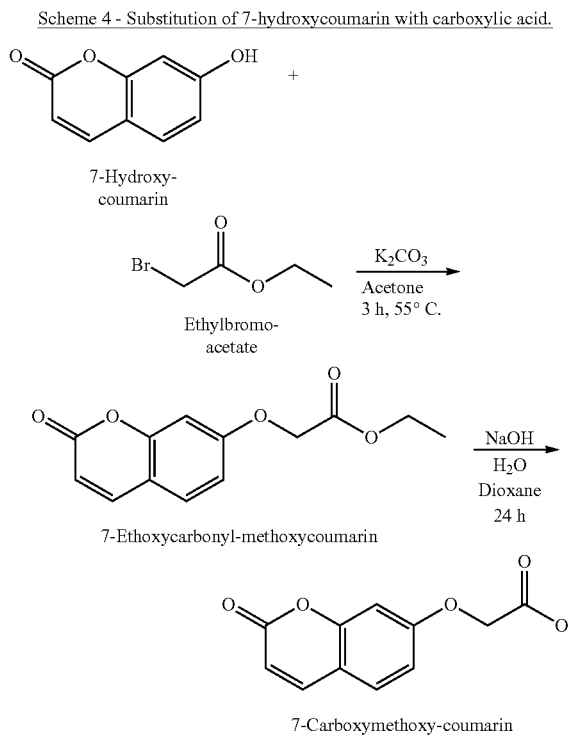

The carboxylic acid reacted with the amines of the dendrimer to form an amide bond. This reaction was run in the presence of 1-ethyl-3-(3-dimethylaminopropyl)carbodiimide (EDC) and N-hydroxysuccinimide (NHS). To substitute the hydroxyl groups of both the dendrimer and the dextran components, the carboxylic acid functional group of the carboxylic acid-substituted 7-hydroxycoumarin was converted to an acyl chloride. The conversion was achieved by contacting the 7-carboxymethoxycoumarin for 3 hours with $SOCl_2$. The hydroxyl groups of both the dendrimer and the dextran components were then allowed to react with the acyl chloride functional group in the presence of triethanolamine (TEA).

The resulting coumarin substitution was determined and verified by H-NMR spectroscopy, MALDI-TOF spectrometry, and potentiometric titration.

Example 2—Evaluation of Reversible Dimerization in Solution

Figure 2A:
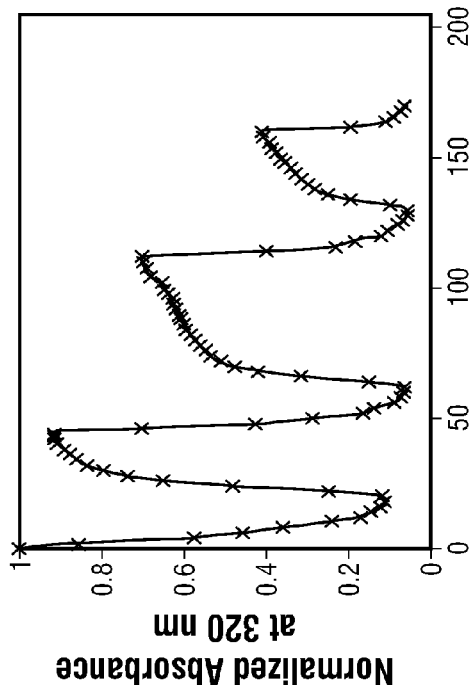
FIG. 2A depicts UV/Vis plots of aqueous 7-ethoxycarbonylmethoxycoumarin upon photoirradiation at a wavelength of 365 nm and 254 nm (inset).
Figure 2B:
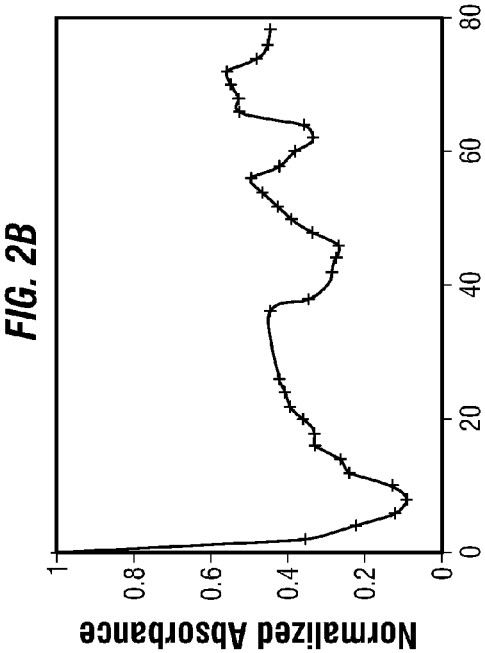
FIG. 2B depicts the absorbance changes of 7-ethoxycarbonylmethoxycoumarin at 320 nm upon alternate irradiation with 365 nm and 254 nm UV light.
Figure 2C:
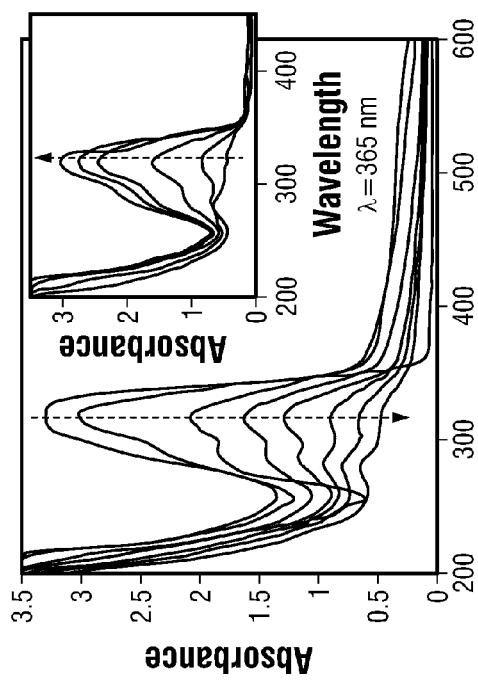
FIG. 2C depicts the absorbance changes of PEG-coumarin at 320 nm upon alternate irradiation with 365 nm and 254 nm UV light.
Figure 2D:
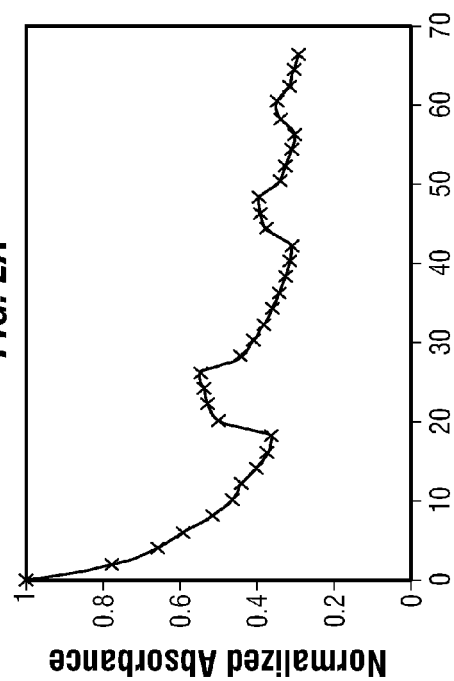
FIG. 2D depicts the absorbance changes of dendrimer-coumarin at 320 nm upon alternate irradiation with 365 nm and 254 nm UV light.

The capacity of the 7-hydroxycoumarin substituents of Example 1 to dimerize reversibly in solution was evaluated by UV/Vis spectroscopy. Absorbance at 320 nm was characteristic of the double bond in the benzopyrone ring of the 7-hydroxycoumarin. Photoirradiation at a wavelength of 365 nm stimulated the dimerization of the coumarin substituents. As a consequence of this photodimerization, the absorbance of the complex at 320 nm decreased. Meanwhile, the UV/Vis absorbance 320 nm increased upon photoirradiation at a wavelength of 254 nm, which indicated the photocleavage of the dimerized coumarin moieties. FIG. 2A and FIG. 2B show the photoreversibility of 7-ethoxycarbonylmethoxycoumarin in water when exposed to a suitable wavelength of UV light. FIG. 2C and FIG. 2D show the behavior of reversibly dimerizable coumarin substituents when attached to polyethylene glycol (PEG) or to a generation 5 PAMAM dendrimer, respectively.

Example 3—Evaluation of Reversible Dimerization of Hydrogel

The reversibility of the coumarin-substituted dendrimers also was demonstrated in the hydrogel state. In this example, a dendrimer having amines on 100% of its surface groups was used, and 30% of the amines were substituted with 7-hydroxycoumarin. The dendrimer was then combined with the dextran component containing aldehydes to form a hydrogel. The dendrimer-dextran hydrogels (which contains coumarin-substituted dendrimer) were fluorescently tagged and submerged in a phosphate buffered saline solution (PBS) to mimic hydrolytic conditions. The fluorescence of the degraded products in the media was quantified and converted to total fluorescence, which indicated the remaining mass in the hydrogel.

The two components of the hydrogels were mixed in a UV chamber and irradiated with UV light at 365 nm for 8 minutes. Two phenomena happen simultaneously: the primary amines of the dendrimer crosslinked with the aldehydes of the dextran, thereby forming imine bonds; and the coumarin substituents of the dendrimer dimerized due to the UV irradiation (see Schemes 1 and 3), thereby increasing the crosslinking density of the hydrogels.

Figure 3A:
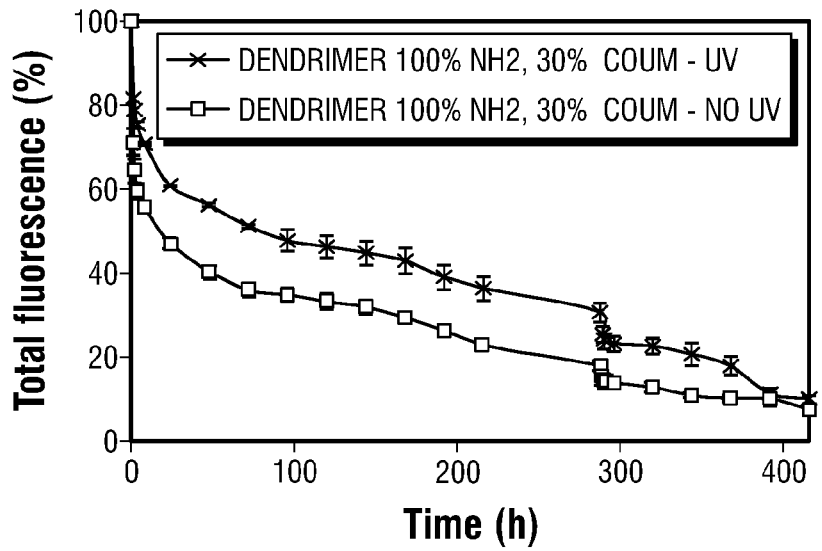
FIG. 3A depicts the degradation of one embodiment of a dendrimer-dextran hydrogel synthesized with coumarin-substituted dendrimer.

As a result, the obtained hydrogels had two different crosslinked structures: first, a fixed imine-type bond between the dextran's aldehydes and the dendrimer's amines, and second, a photosensitive coumarin-type crosslinking between coumarin moieties. The plot in FIG. 3A clearly shows the impact of this second crosslinked structure with a significant difference in the degradation rates of the UV irradiated samples in comparison with the control samples that were not irradiated with UV light, during the first 280 hours of the experiment.

Due to the initial irradiation, the coumarin substituents dimerized and increased the crosslinking density of the hydrogels, which enhanced the resistance of the gels to hydrolytic degradation. After 12 days (288 hours), these samples were irradiated with UV light at 254 nm for 8 minutes in order to cleave the coumarin dimers and thus accelerate their degradation. After 4 days, the remaining mass of the irradiated hydrogels reached the level of non-irradiated control samples, corroborating the cleavage of the coumarin dimers.

The reduction in mass seen between 288 hours and 296 hours in both irradiated and control samples was mainly due to the erosion of the gels because of the frequent change of media during the first time intervals after cleavage (1 h, 2 h, 4 h, 8 h, 24 h).

Figure 3B:
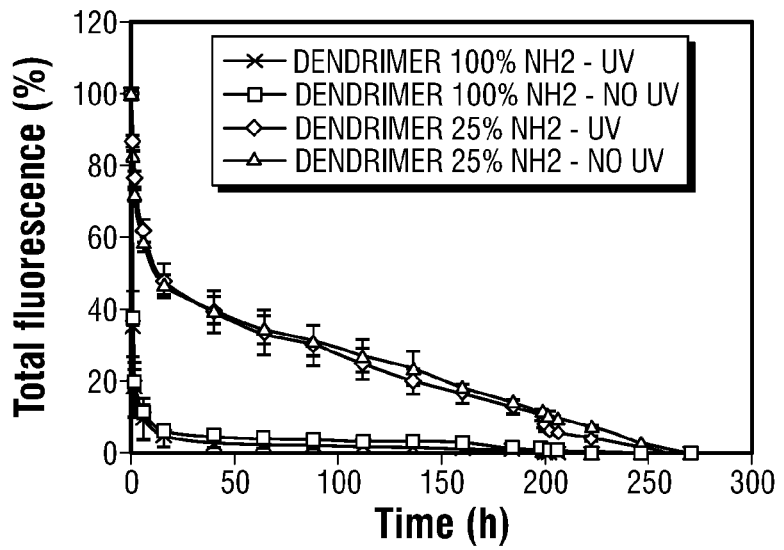
FIG. 3B depicts the degradation of two embodiments of a dendrimer-dextran hydrogel.
Figure 3C:
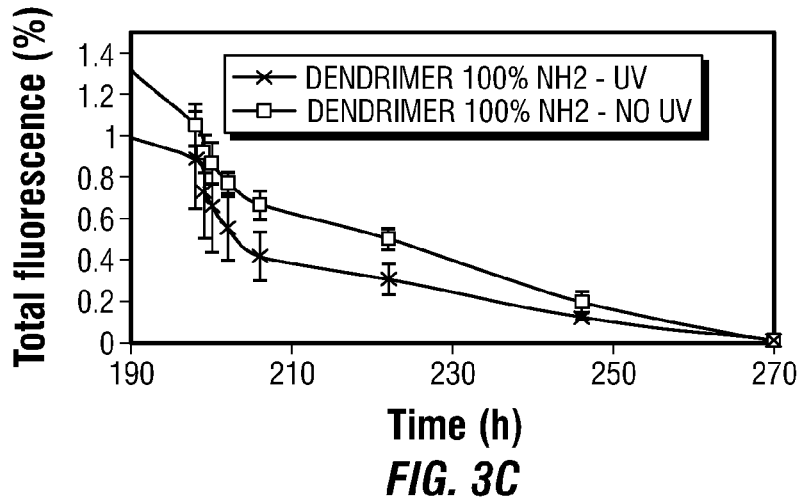
FIG. 3C depicts a zoomed in view of the region of irradiation at 254 nm of FIG. 3B.

In order to verify that the variations in the degradation were due to the dimerization and cleavage of the coumarin substituents and not to the modification of the properties of the dendrimer-dextran hydrogels caused by the irradiation of UV light, several hydrogels were synthesized using a dendrimer that did not include the coumarin substituents. The percentages of amines on the surface groups of these coumarins are shown in FIG. 3B and FIG. 3C, which depict the degradation of the hydrogels.

In this experiment, fast degrading hydrogels made of dendrimer having amines on 25% of its surface groups were also used to test their degradation over a short period of time. Half of the samples were irradiated with UV light at 365 nm and 254 nm at times of 0 h and 198 h, respectively. The irradiation at 365 nm did not cause any significant change in the degradation of the hydrogels. The irradiation at 254 nm seemed to reduce the mass of the hydrogels made of dendrimer having amines on 25% of their surface groups during the first time points after the irradiation. However, the degradation rate tracked that of the non-irradiated homologues after one day.

Example 4—On-Demand Quick Removal

Hydrolytic Degradation v. Enzymatic Degradation.

The formation of an imine bond from an aldehyde and a primary amine is a reversible reaction (Meyer, C. D. et al., CHEM. SOC. REV. 2007, 36, 1705). However, in the absence of aqueous media, the reaction is thermodynamically favored towards the formation of the imine product. As a result of this reaction, a molecule of water is released. In aqueous media, the excess of water shifts the thermodynamic equilibrium towards the reagents (aldehyde and amine) and, therefore, hydrolytic degradation occurs. Nevertheless, the complete degradation of the material is a slow process that can take several days or months, depending on the crosslinking density. The following scheme depicts the imine bond formation.

Scheme 5 - Imine Bond Formation.

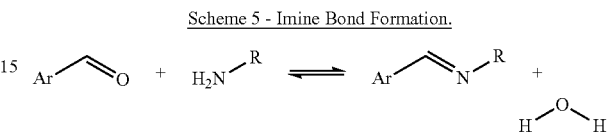

Figure 4:
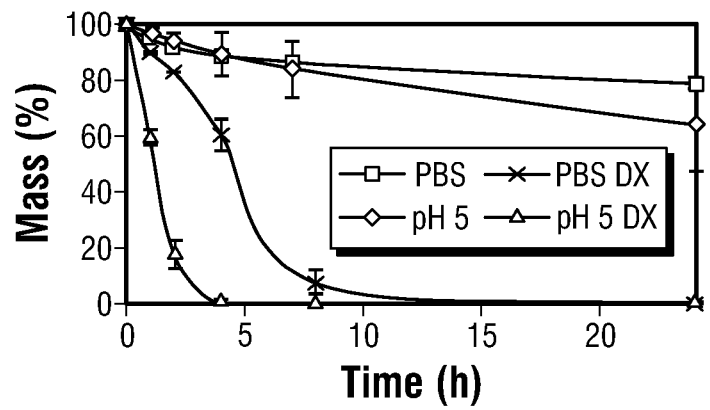
FIG. 4 depicts the enzymatic degradation of embodiments of a dextran-dendrimer hydrogel with dextranase.
Figure 5:
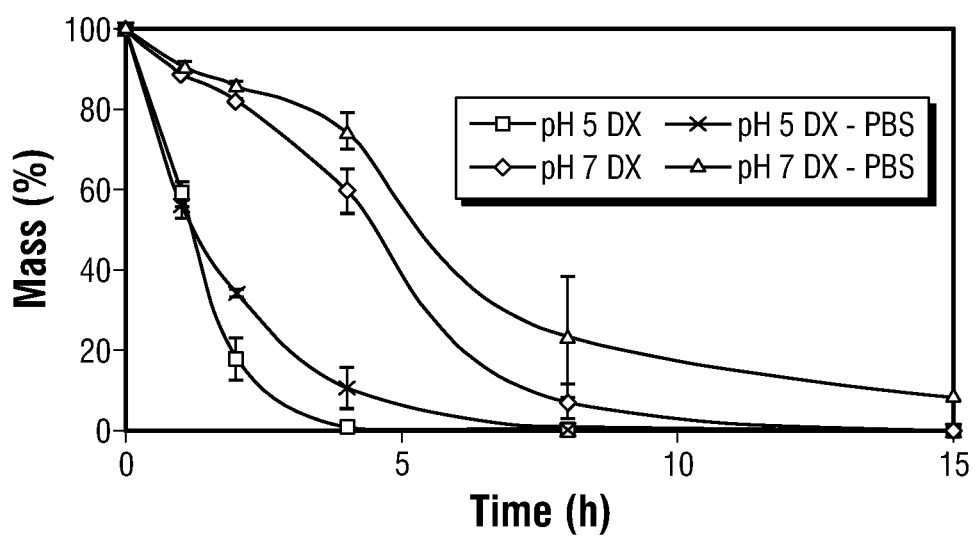
FIG. 5 depicts the initial enzymatic degradation of embodiments of a dextran-dendrimer hydrogel with dextranase (DX) followed by hydrolysis in phosphate buffer saline (PBS) after 1 hour (DX–PBS).

To facilitate on-demand cleavage for easy material removal, dextran was enzymatically degraded by dextranases, which are commonly used in the food industry and are considered biocompatible. Dextranases cleave the dextran alpha-1,6 linkages and therefore facilitate the erosion of the material by the media (Rodriguez, E., et al. SUGAR TECH 2007, 11(2), 124). Some studies in the literature have investigated the conditions of the hydrolytic degradation of dextran using dextranase (Jung, S. W. et al. J. OF MICROENCAPSULATION 2005, 22(8), 901; Kurisawa, et al. J. BIOMATER. SCI. POLYMER ED. 1997, 8, 691). The degradation of the dextran-dendrimer hydrogels at the optimal conditions for dextranases (5 U/mL, pH 5 and 7) were investigated. The degradation, as shown in FIG. 4 and FIG. 5, the degradation was greatly enhanced with the presence of enzymes. The degradation was more accentuated at pH of 5 due to the effect of acid hydrolysis.

Acidic Degradation of Dextran.

Figure 6:
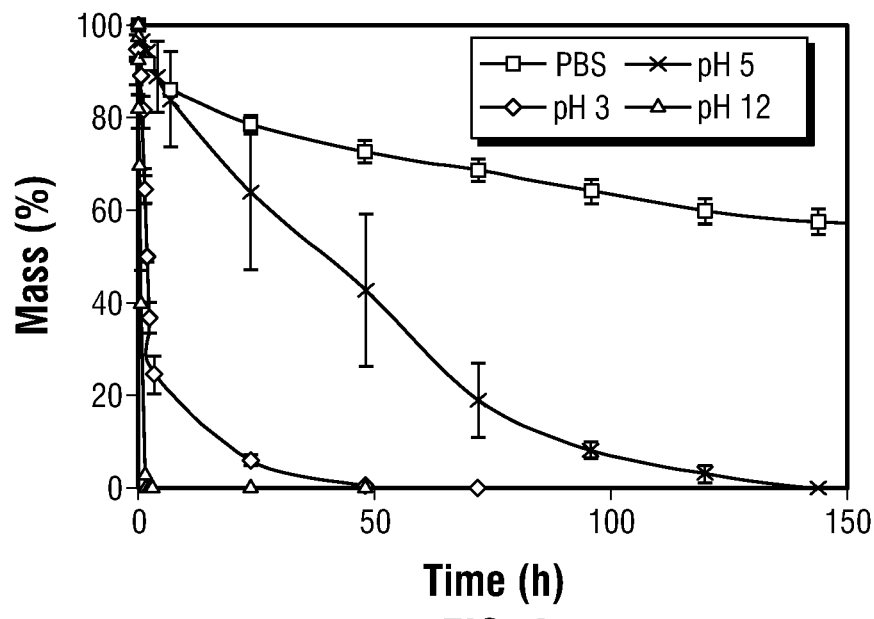
FIG. 6 depicts the hydrolysis of an embodiment of a dextran-dendrimer hydrogel at different pH conditions.
Figure 7:
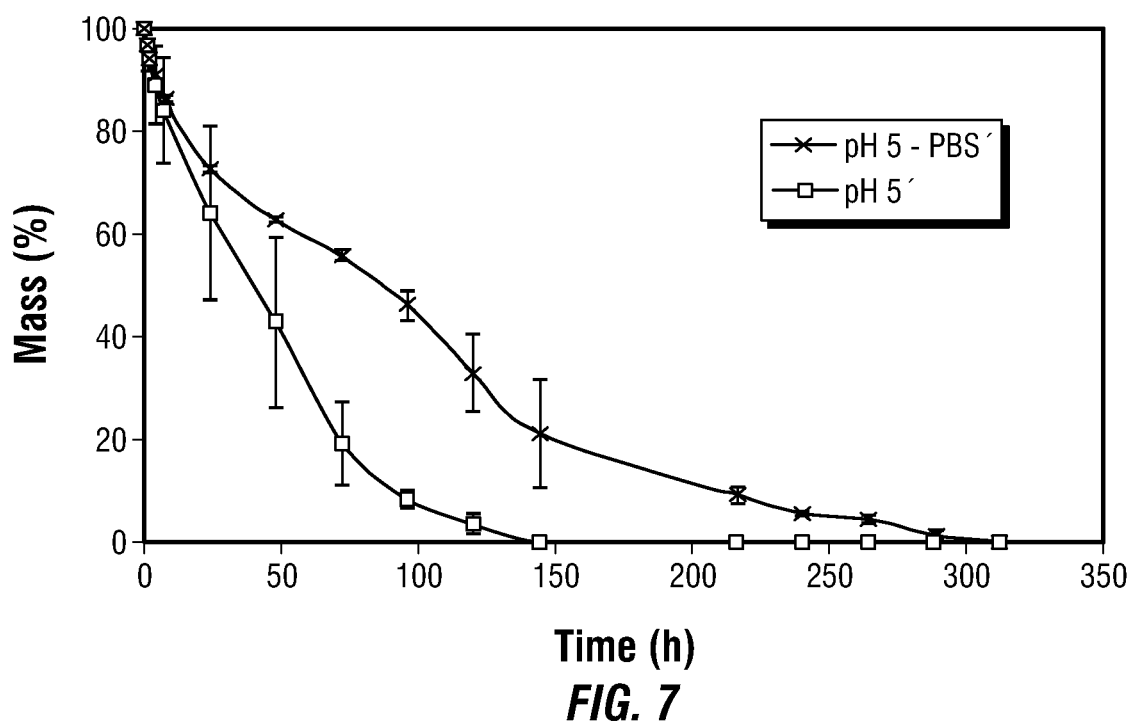
FIG. 7 depicts the initial acid hydrolysis of an embodiment of a dextran-dendrimer hydrogel at pH 5 followed by hydrolysis in PBS after 1 hour (pH 5–PBS).

Aqueous solutions of dextran are stable in the pH range of from about 4 to about 10. Outside of this range, however, dextran undergoes rapid degradation. Therefore, the hydrolysis of dextran-dendrimer hydrogels is enhance at pH lower than about 5 and higher than about 10 (see FIG. 6 and FIG. 7). The dendrimer used for FIGS. 6 and 7 was a G5-25-12.55 PAMAM dendrimer, i.e., a 12.55% (by weight) solution of G5 PAMAM dendrimer having 25% of its surface groups The dextran used for FIG. 7 was a D40-50-7.5 dextran, i.e., a 7.5% (by weight) solution of 40 kDalton dextran having 50% of its hydroxyl groups converted to aldehydes.

Some of the dendrimers provided herein have a high buffering capacity in acidic conditions due to the unprotonated surface amines, which are able to capture protons and, therefore, lower the acidity of the media. In basic conditions, however, some of the dendrimers have lower buffering capability. Therefore, when dextran is combined with dendrimer to form a hydrogel, the hydrolysis is greater at basic pH rather than in acidic conditions.

Trans-Amination (Ethylene Diamine pKa to Avoid Crosslinking).

As previously stated, the imine bond is reversible. However, the imine form is thermodynamically and kinetically favored. Typically, when different types of amines are present in a material or environment containing aldehydes, there is competition for the imine formation that will be determined by the nucleophilic capability of the amines.

Generally, the type of amine that shows greater affinity for aldehydes will form all of, or most of, the imine bonds. However, if a strong amine nucleophile is added to a material that has previously formed imines with amines having moderately strong nucleophilic character, there will be an exchange of amines in the imine bonds and the material will change its crosslinking structure. Additionally, if the new amine (strong nucleophile) is a small molecule able to reach all of the confinements of the material, then the formation of the new type of imines is enhanced.

Figure 8:
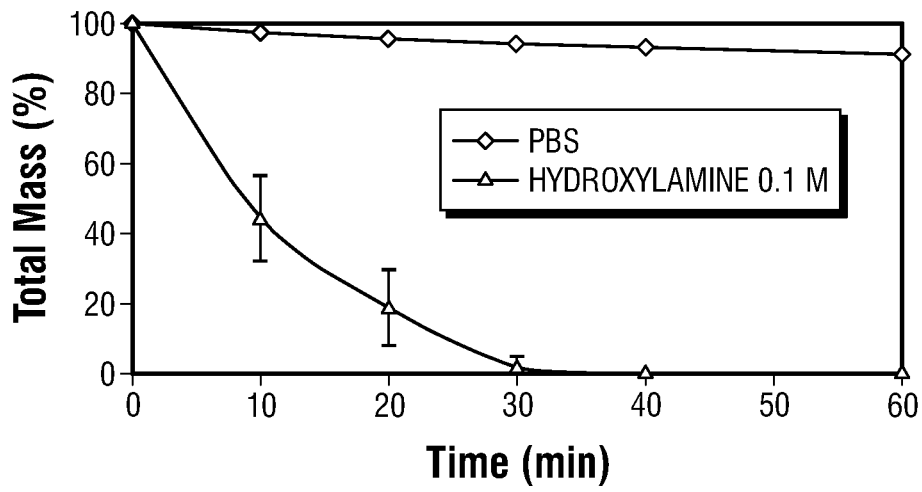
FIG. 8 depicts the degradation of an embodiment of a dextran-dendrimer hydrogel with hydroxylamine.

Hydroxylamine is one of the smallest existing amines and one of the greatest nucleophiles. The combination of these two properties gives hydroxylamine the ability to interfere very effectively in all imine bonds and substitute the amines. When dextran-dendrimer hydrogels were placed in PBS media with 0.1 M hydroxylamine, the degradation was greatly enhanced. After 10 minutes, only 40% of the material was present. After 10 minutes of degradation with hydroxylamine, the dextran-dendrimer hydrogels were completely degraded (see FIG. 8).

Figure 9:
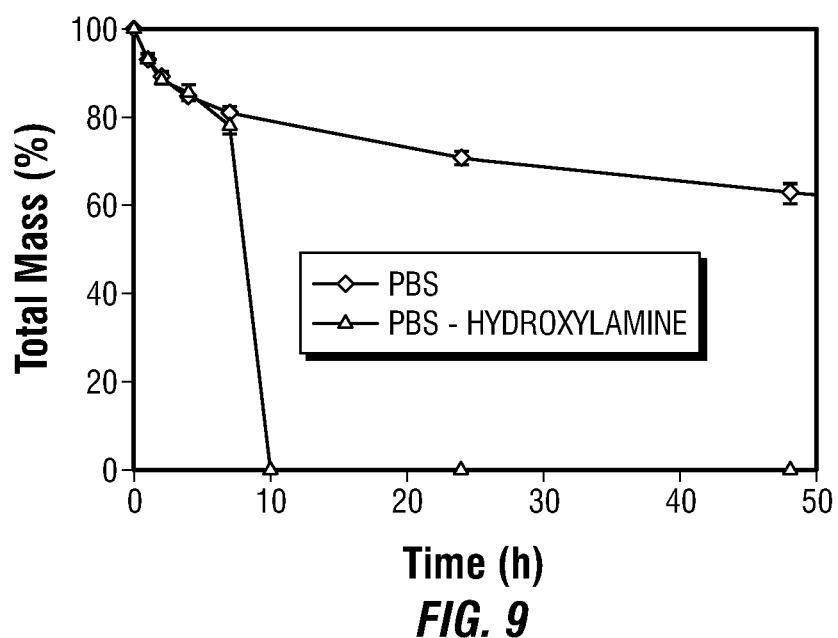
FIG. 9 depicts the initial hydrolysis of an embodiment of a dextran-dendrimer hydrogel in PBS followed by a complete and fast degradation with hydroxylamine after 7 hours (PBS-hydroxylamine).

Therefore, injection of 0.1 M hydroxylamine into the cured hydrogel enhanced the degradation significantly, which allowed for the easy removal of the adhesive. This was demonstrated by placing 8 dextran-dendrimer hydrogels in PBS media for 8 h. Half of the samples were placed in PBS 0.1 M hydroxylamine media where the other half remained in regular PBS. In the first case, the samples were totally degraded at the next time point as opposed to the other hydrogels in PBS that remained solid for several days (FIG. 9). The dendrimers and dextran used for FIG. 9 were the same as those used for FIGS. 6 and 7.

While the present invention may be embodied in many different forms, disclosed herein are specific illustrative embodiments thereof that exemplify the principles of the invention. It should be emphasized that the present invention is not limited to the specific embodiments illustrated.

We claim:

1. A method for treating, adhering, or sealing biological tissue, the method comprising:
    providing a first solution comprising a polymer component, wherein the polymer component comprises a polymer having three or more aldehyde groups;
    providing a second solution comprising a dendrimer component, wherein the dendrimer component comprises a dendrimer having at least 2 branches with one or more surface groups;
    wherein at least one of the polymer and dendrimer is substituted with one or more substituents capable of photoreversible dimerization;
    combining the first and second solutions together to produce an adhesive formulation and contacting one or more biological tissues with the adhesive formulation;
    allowing the adhesive formulation to cure in contact with the one or more biological tissues; and
    contacting the adhesive formulation with light having a wavelength sufficient to dimerize the substituent capable of photoreversible dimerization.

2. The method of claim 1, wherein allowing the adhesive formulation to cure and contacting the adhesive formulation with light are performed simultaneously.

3. The method of claim 1, further and subsequently comprising contacting the adhesive formulation with light having a wavelength sufficient to reverse the dimerization of the substituents capable of photoreversible dimerization.

4. The method of claim 1, wherein the method further comprises contacting the adhesive formulation with an enzyme effective to degrade the polymer.

5. The method of claim 4, wherein the enzyme is a dextranase and the polymer is dextran.

6. The method of claim 1, wherein the method further comprises contacting the adhesive formulation with an amine effective to alter the equilibrium of imine bond formation.

7. The method of claim 6, wherein the amine comprises hydroxylamine.

8. The method of claim 1, wherein the method further and subsequently comprises altering the pH of the adhesive formulation in an amount effective to facilitate degradation of the polymer.

9. The method of claim 1, wherein the polymer is dextran.

10. The method of claim 1, wherein the dendrimer is a G5 PAMAM dendrimer.

11. The method of claim 1, wherein 100% of the surface groups comprise at least one primary or secondary amine.

12. The method of claim 1, wherein less than 75% of the surface groups comprise at least one primary or secondary amine.

* * * * *